US010048179B2

(12) United States Patent
Lai et al.

(10) Patent No.: US 10,048,179 B2
(45) Date of Patent: Aug. 14, 2018

(54) DETERMINING ROCK PROPERTIES

(71) Applicant: Saudi Arabian Oil Company, Dhahran OT (SA)

(72) Inventors: Bitao Lai, Katy, TX (US); Hui Li, Lafayette, LA (US); Hui-Hai Liu, Katy, TX (US); Yanhui Han, Katy, TX (US)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/097,924

(22) Filed: Apr. 13, 2016

(65) Prior Publication Data

US 2017/0299485 A1    Oct. 19, 2017

(51) Int. Cl.
*G01D 1/16* (2006.01)
*G01N 3/08* (2006.01)
*G01N 33/24* (2006.01)

(52) U.S. Cl.
CPC .............. *G01N 3/08* (2013.01); *G01N 33/24* (2013.01)

(58) Field of Classification Search
CPC .................................. G01N 33/24; G01N 3/08
USPC .......................................................... 73/790
See application file for complete search history.

(56) References Cited

U.S. PATENT DOCUMENTS

| | | | |
|---|---|---|---|
| 4,444,058 A * | 4/1984 | Ratigan | G01N 3/08 73/834 |
| 4,587,739 A * | 5/1986 | Holcomb | G01B 7/12 33/550 |
| 5,193,396 A * | 3/1993 | Gorski | G01N 3/04 73/831 |
| 5,757,473 A | 5/1998 | Kanduth et al. | |
| 5,869,750 A | 2/1999 | Onan | |
| 2005/0103118 A1 | 5/2005 | Workman | |
| 2013/0228019 A1 * | 9/2013 | Meadows | G01N 3/08 73/821 |
| 2013/0233536 A1 * | 9/2013 | Alqam | G01N 3/00 166/250.01 |
| 2015/0152724 A1 * | 6/2015 | Amendt | G01N 1/04 73/152.01 |
| 2016/0103047 A1 | 4/2016 | Liu | |
| 2016/0103049 A1 | 4/2016 | Liu | |

FOREIGN PATENT DOCUMENTS

| | | |
|---|---|---|
| CN | 101819111 | 12/2011 |
| CN | 1621803 B | 5/2012 |
| CN | 102183410 B | 5/2014 |
| WO | 2012/051647 | 4/2012 |

OTHER PUBLICATIONS

Pollard, D. D.and Fletcher, R.C., "Fundamentals of Structural Geology," Cambridge University Press, Sep. 1, 2005; p. 291.

(Continued)

*Primary Examiner* — Max Noori
(74) *Attorney, Agent, or Firm* — Fish & Richardson P.C.

(57) ABSTRACT

Techniques for determining rock properties include exerting a compressive load with a test apparatus across a rock sample that includes a specified length-to-diameter ratio; measuring, with a strain gauge, a strain on the rock sample during the compressive loading; determining, based at least in part on the compressive load, a mechanical property of the rock sample; and determining, based at least in part on the measured strain and the compressive load, an elastic property of the rock sample.

28 Claims, 10 Drawing Sheets

(56) References Cited

OTHER PUBLICATIONS

Li et al., "The Brazilian Disc Test for Rock Mechanics Applications: Review and New Insights," Rock Mech Rock Eng, published in 2013, 46: pp. 269-287.

Liu, "Elastic Constants Determination and Deformation Observation Using Brazilian Disk Geometry," Experimental Mechanics, published in 2010, 50: pp. 1025-1039.

Wang et al., "The Flattened Brazilian Disc Specimen Used for Testing Elastic Modulus, Tensile Strength and Fracture Toughness of Brittle Rocks: Analytical and Numerical Results," Int J Rock Mech Min Sci 41(2): pp. 245-253.

Ye et al., "Estimation of the Tensile Elastic Modulus using Brazilian disc by Applying Diametrically Opposed Concentrated Loads," International Journal of Rock Mechanics & Mining Sciences. 46, published in 2009, 568-576.

Bazant et al., "Size Effect in Brazilian Split-Cylinder Tests: Mesurements and Fracture Analysis," ACI Materials Journal, vol. 88, No. 3, May 31, 1991; pp. 325-332.

International Search Report and Written Opinion issued in International Application No. PCT/US2017/026927 dated Jul. 11, 2017; 14 pages.

\* cited by examiner

DETERMINING ROCK PROPERTIES

TECHNICAL FIELD

This disclosure relates to determining rock properties and, more particularly, determining tensile strength and elastic rock properties with a single test.

BACKGROUND

Rock mechanical properties are important to many practical applications related to reservoir characterization and modeling. Certain rock mechanical properties may inform a geologist, engineer or driller about tensile properties of a particular rock formation or sample. Some rock properties are stress dependent.

SUMMARY

The present disclosure describes a rock sample test that may determine elastic and mechanical properties of the rock sample during and with a single test. For example, in some aspects, the rock sample test may be a Brazilian test according to American Society for Testing and Materials (ASTM) Standard D3967-08 and includes a compressive test of a disc-shaped rock sample with known geometries. In some aspects, the elastic properties may be, for example, Young's modulus or Poisson's ratio, while the mechanical properties may include tensile strength, among others.

In a general implementation, a method for determining rock properties includes exerting a compressive load with a test apparatus across a rock sample that includes a specified length-to-diameter ratio; measuring, with a strain gauge, a strain on the rock sample during the compressive loading; determining, based at least in part on the compressive load, a mechanical property of the rock sample; and determining, based at least in part on the measured strain and the compressive load, an elastic property of the rock sample.

In an aspect combinable with the general implementation, the specified length-to-diameter ratio is between 0.2 and 0.75.

In another aspect combinable with any of the previous aspects, the test apparatus includes a Brazilian test apparatus.

In another aspect combinable with any of the previous aspects, the strain gauge is coupled to an axial surface of the rock sample.

In another aspect combinable with any of the previous aspects, measuring a strain on the rock sample during the compressive loading includes measuring an incremental axial strain on the rock sample during a compressive load increment with a first strain gauge; and measuring an incremental radial strain on the rock sample during the compressive load increment with a second strain gauge.

In another aspect combinable with any of the previous aspects, determining, based at least in part on the measured strain and the compressive load, the elastic property of the rock sample includes determining a first coefficient based at least in part on the diameter of the rock sample, the length of the rock sample, and an effective length of the first and second strain gauges; determining a second coefficient based at least in part on the diameter of the rock sample, the length of the rock sample, and the effective length of the first and second strain gauges; and determining the elastic property of the rock sample based at least in part on the measured incremental axial and radial strains on the rock sample, the first and second coefficients, and the compressive loading increment.

In another aspect combinable with any of the previous aspects, determining, based at least in part on the measured strain and the compressive load, the elastic property of the rock sample includes determining a Young's modulus of the rock sample based on at least one of $$E = \frac{\Delta P}{\Delta \varepsilon_x}(-F + \nu G), \quad \text{(i)}$$

where E is stress dependent Young's modulus of the rock sample, $\Delta P$ is a compressive loading increment, $\Delta \epsilon_x$ is an incremental radial strain, $\nu$ is Poisson's ratio of the rock sample, F is a first coefficient, and G is a second coefficient; or $$E = \frac{P}{\varepsilon_x}(-F + \nu G), \quad \text{(ii)}$$

where E is Young's modulus of the rock sample, P is a particular compressive load, $\epsilon_x$ is a radial strain at the particular compressive load, $\nu$ is Poisson's ratio of the rock sample, F is the first coefficient, and G is the second coefficient.

In another aspect combinable with any of the previous aspects, determining, based at least in part on the measured strain and the compressive load, the elastic property of the rock sample includes determining Poisson's ratio of the rock sample based on at least one of $$\nu = \frac{\left(\frac{\Delta \varepsilon_x}{\Delta \varepsilon_y}\right) G + F}{\left(\frac{\Delta \varepsilon_x}{\Delta \varepsilon_y}\right) F + G}, \quad \text{(i)}$$

where $\nu$ is stress dependent Poisson's ratio of the rock sample, $\Delta \epsilon_x$ is an incremental radial strain, $\Delta \epsilon_y$ is an incremental axial strain, F is a first coefficient, and G is a second coefficient; or $$\nu = \frac{\left(\frac{\varepsilon_x}{\varepsilon_y}\right) G + F}{\left(\frac{\varepsilon_x}{\varepsilon_y}\right) F + G}, \quad \text{(ii)}$$

where $\nu$ is Poisson's ratio of the rock sample, $\epsilon_x$ is a radial strain at a particular compressive load on the rock sample, $\Delta \epsilon_y$ is an axial strain at the particular compressive load on the rock sample, F is the first coefficient, and G is the second coefficient.

In another aspect combinable with any of the previous aspects, the mechanical property includes at least one of a tensile strength or a brittleness of the rock sample.

In another aspect combinable with any of the previous aspects, the strain gauge includes a linear variable differential transformer (LVDT).

In another general implementation, a rock property test system includes a load cell configured to exert a compressive load across a rock sample; at least one strain gauge positioned to measure a strain on the rock sample during the compressive loading; and a control system communicably coupled to the load cell and the at least one strain gauge and configured to perform operations including: controlling the load cell to exert an incremental compressive load on the rock sample; receiving a measured strain on the rock sample, based on the incremental compressive load, from the at least one strain gauge; determining, based at least in part on the incremental compressive load, a mechanical property of the rock sample; and determining, based at least in part on the measured strain and the incremental compressive load, an elastic property of the rock sample.

In an aspect combinable with the general implementation, the rock sample includes a length-to-diameter ratio between 0.2 and 0.75.

In another aspect combinable with any of the previous aspects, the load cell includes a Brazilian test apparatus.

In another aspect combinable with any of the previous aspects, the strain gauge is configured to attach to an axial surface of the rock sample.

In another aspect combinable with any of the previous aspects, the strain gauge includes a first strain gauge configured to measure an incremental axial strain on the rock sample during the incremental compressive load; and a second strain gauge configured to measure an incremental radial strain on the rock sample during the incremental compressive load.

In another aspect combinable with any of the previous aspects, the control system is configured to perform further operations including determining a first coefficient based at least in part on the diameter of the rock sample, the length of the rock sample, and an effective length of the first and second strain gauges; determining a second coefficient based at least in part on the diameter of the rock sample, the length of the rock sample, and the effective length of the first and second strain gauges; and determining the elastic property of the rock sample based at least in part on the measured incremental axial and radial strains on the rock sample, the first and second coefficients, and the incremental compressive load.

In another aspect combinable with any of the previous aspects, the operation of determining, based at least in part on the measured strain and the compressive load, the elastic property of the rock sample includes determining a Young's modulus of the rock sample based on at least one of $$E = \frac{\Delta P}{\Delta \varepsilon_x}(-F + \nu G), \tag{i}$$

where t is stress dependent Young's modulus of the rock sample, $\Delta P$ is a compressive loading increment, $\Delta \varepsilon_x$ is an incremental radial strain, $\nu$ is Poisson's ratio of the rock sample, F is a first coefficient, and G is a second coefficient; or $$E = \frac{P}{\varepsilon_x}(-F + \nu G), \tag{ii}$$

where E is Young's modulus of the rock sample, P is a particular compressive load, $\varepsilon_x$ is a radial strain at the particular compressive load, $\nu$ is Poisson's ratio of the rock sample, F is the first coefficient, and G is the second coefficient.

In another aspect combinable with any of the previous aspects, the operation of determining, based at least in part on the measured strain and the compressive load, the elastic property of the rock sample includes determining Poisson's ratio of the rock sample based on at least one of $$\nu = \frac{\left(\frac{\Delta \varepsilon_x}{\Delta \varepsilon_y}\right)G + F}{\left(\frac{\Delta \varepsilon_x}{\Delta \varepsilon_y}\right)F + G}, \tag{i}$$

where $\nu$ is stress dependent Poisson's ratio of the rock sample, $\Delta \varepsilon_x$ is an incremental radial strain, $\Delta \varepsilon_y$ is an incremental axial strain, F is a first coefficient, and G is a second coefficient; or $$\nu = \frac{\left(\frac{\varepsilon_x}{\varepsilon_y}\right)G + F}{\left(\frac{\varepsilon_x}{\varepsilon_y}\right)F + G}, \tag{ii}$$

where $\nu$ is Poisson's ratio of the rock sample, $\varepsilon_x$ is a radial strain at a particular compressive load on the rock sample, $\Delta \varepsilon_y$ is an axial strain at the particular compressive load on the rock sample, F is the first coefficient, and G is the second coefficient.

In another aspect combinable with any of the previous aspects, the mechanical property includes at least one of a tensile strength or a brittleness of the rock sample.

In another general implementation, a method includes performing a Brazilian test on a rock sample, the Brazilian test including exerting an incremental compressive load across a rock sample, and determining, based at least in part on the incremental compressive load, a mechanical property of the rock sample; measuring, with a strain gauge, a strain on the rock sample during the incremental compressive load; and determining, based at least in part on the measured strain and the incremental compressive load, an elastic property of the rock sample.

In an aspect combinable with the general implementation, the rock sample includes a disc having a length-to-diameter ratio between 0.2 and 0.75.

In another aspect combinable with any of the previous aspects, the strain includes an axial strain and a radial strain, and determining the elastic property of the rock sample includes determining the elastic property of the rock sample based at least in part on the axial and radial strains on the rock sample and the incremental compressive load.

In another aspect combinable with any of the previous aspects, determining the elastic property of the rock sample based at least in part on the axial and radial strains on the rock sample and the incremental compressive load includes determining the elastic property of the rock sample based at least in part on the axial and radial strains on the rock sample, the incremental compressive load, and two predetermined constants.

In another aspect combinable with any of the previous aspects, the two predetermined constants are based at least in part on a diameter of the rock sample, a length of the rock sample, and an effective length of the strain gauge.

Implementations according to the present disclosure may include one or more of the following features. For example, tensile and elastic parameters of a rock sample can be estimated in a single compression test, such as a Brazilian test. As another example, tensile and elastic properties of a rock sample may be determined by a widely-accepted and used test procedure, for example, the Brazilian test procedure. As yet another example, implementations described in the present disclosure may minimize the requirement of multiple core samples to determine tensile and elastic properties. For example, implementations may determine, in a single test, a tensile strength, a Young's modulus, a Poisson's ratio, a stress-strain curve, brittleness and toughness of a rock sample. Further, implementations may allow for core samples to be tested that have a range of diameters. As another example, numerical inversions are not required for testing the rock sample to determine tensile and elastic properties, and thus may be easier to implement in practical applications. As another example, the described implementations do not require any extra mechanical testing equipment and can be incorporated in conventional compression test equipment.

The details of one or more implementations of the subject matter described in this disclosure are set forth in the accompanying drawings and the description. Other features, aspects, and advantages of the subject matter will become apparent from the description, the drawings, and the claims.

DETAILED DESCRIPTION

The present disclosure describes a rock sample test that may determine elastic and mechanical properties of the rock sample during and with a single test. For example, in some aspects, the rock sample test may be a Brazilian test according to American Society for Testing and Materials (ASTM) Standard D3967-08 and includes a compressive test of a disc-shaped rock sample with known geometries. In some aspects, the elastic properties may be, for example, Young's modulus or Poisson's ratio, while the mechanical properties may include tensile strength, among others.

Figure 1:
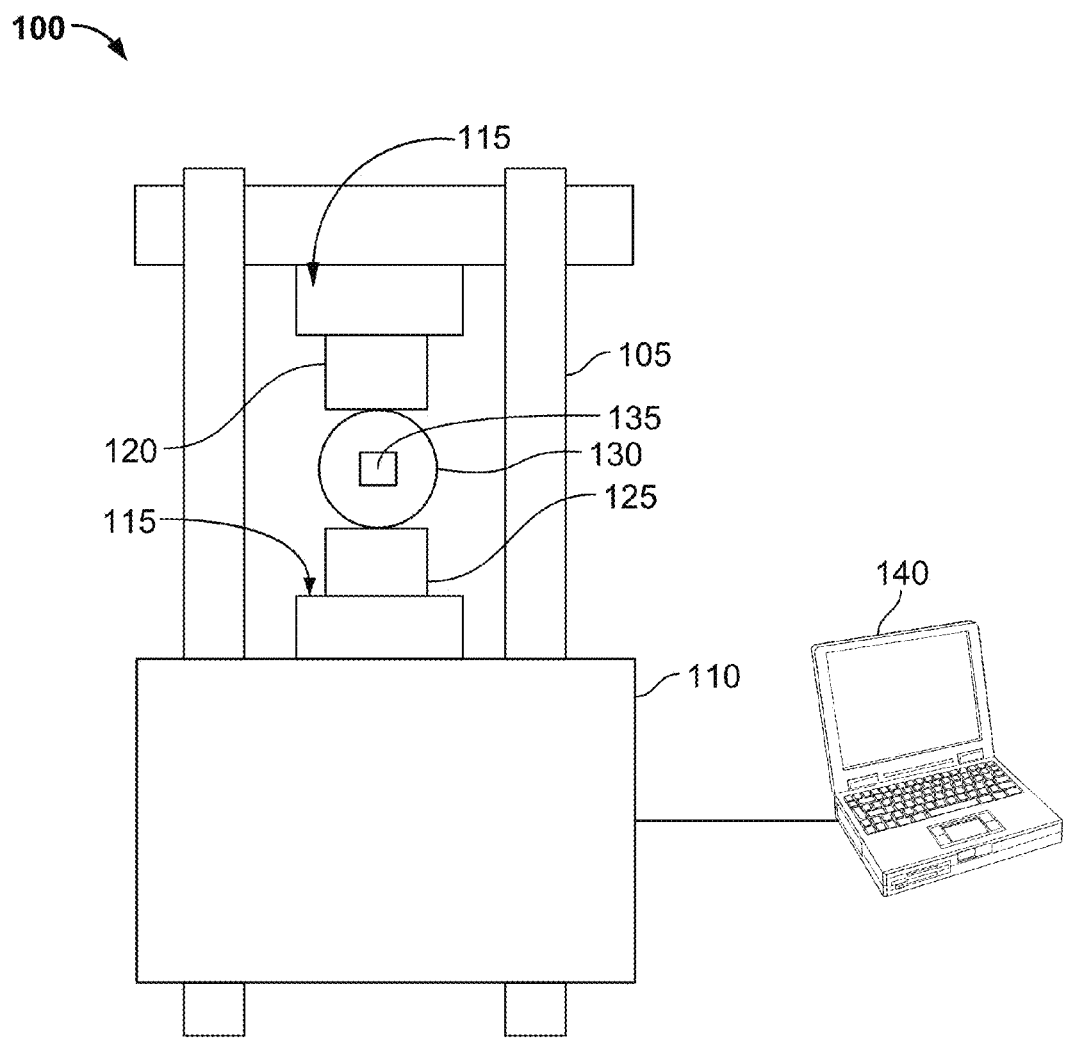
FIG. 1 is a schematic illustration of a testing apparatus for determining one or more rock mechanical properties according to the present disclosure.

FIG. 1 is a schematic illustration of a testing apparatus 100 for determining one or more rock mechanical properties. Testing apparatus 100, generally may be operated to perform compressive tests, including indirect tensile strength test, or a splitting test, on a rock sample (for example, an isotropic rock sample or an anisotropic rock sample), such as the rock sample 130 shown in FIG. 1. For example, in some implementations, the testing apparatus 100 may perform a Brazilian test on the rock sample 130. The Brazilian test, for example, is a laboratory test for indirect measurement of tensile strength of the rock sample 130 or other hardened material (for example, concrete, cement). Generally, in the Brazilian test, a disc-shaped rock sample (rock sample 130) is loaded by two opposing platens in contact with opposed portions of a radial surface of the rock sample 130. A compressive load is incrementally increased on the rock sample 130 until the rock sample 130 fails (in other words, splits), after which, mechanical properties of the rock sample (for example, tensile strength, brittleness) may be calculated or determined. Testing criteria such as increment of load, rate of loading, for instance, may be adjusted from test to test.

The example implementation of the testing apparatus 100, which may also be referred to in this disclosure as a Brazilian test apparatus, includes a load frame 105 positioned on a base 110 and arranged to support load cells 115. The illustrated load cells 115 are positioned such that an upper platen 120 and a lower platen 125 are mounted in between the cells 115. The upper platen 120 and the lower platen 125 are separated, during non-operation of the testing apparatus 100, to allow the rock sample 130 to be placed between the platens 120 and 125. When in non-compressive contact with the platens 120 and 125, a radial surface of the rock sample 130 is in contact with the upper and lower platens 120 and 125, respectively. Thus, in FIG. 1, an axial surface, defined by a diameter of the rock sample 130, is perpendicular to the contacting surfaces of the platens 120 and 125 (in other words, the surfaces of the platens 120 and 125 that contact the radial surface of the rock sample 130).

In the illustrated implementation, one or more strain gauges 135 are shown as engaged (for example, with adhesive) with the axial surface of the rock sample 130. The one or more strain gauges 135, generally, may be any device that measures strain on the rock sample 130 during a compressive loading operation. The strain gauge 130, for example, may be a linear variable differential transformer (LVDT) or other strain gauge that measures strain based on an electrical conductance of a deformable electrical conductor. In some implementations, two strain gauges 135 may be attached to the rock sample 130 to measure axial and radial strain, respectively.

The testing apparatus 100, as shown, includes a control system 140. Although shown separately from the load cells 115 and other portions of the testing apparatus 100, the control system 140 may be built into, or integrated with, the testing apparatus 100. In any event, the control apparatus 140 may be communicably coupled to one or more components of the testing apparatus 100, such as the load cells 115, and the strain gauge(s) 135. The control system 140, generally, may control operation of the load cells 115 (for example, rate of loading, loading compressive force) to exert a compressive load on the rock sample 130. The control system 140 may also receive data from, for example, the load cells 115 (compressive load values, travel distance of the platens 120 and 125 during loading) and the strain gauge(s) 135 (for example, measured axial and radial strain on the rock sample 130). The control system 140 may be a microprocessor based controller, an electrical or electromechanical based controller, a pneumatic or hydraulic based controller.

Figure 2:
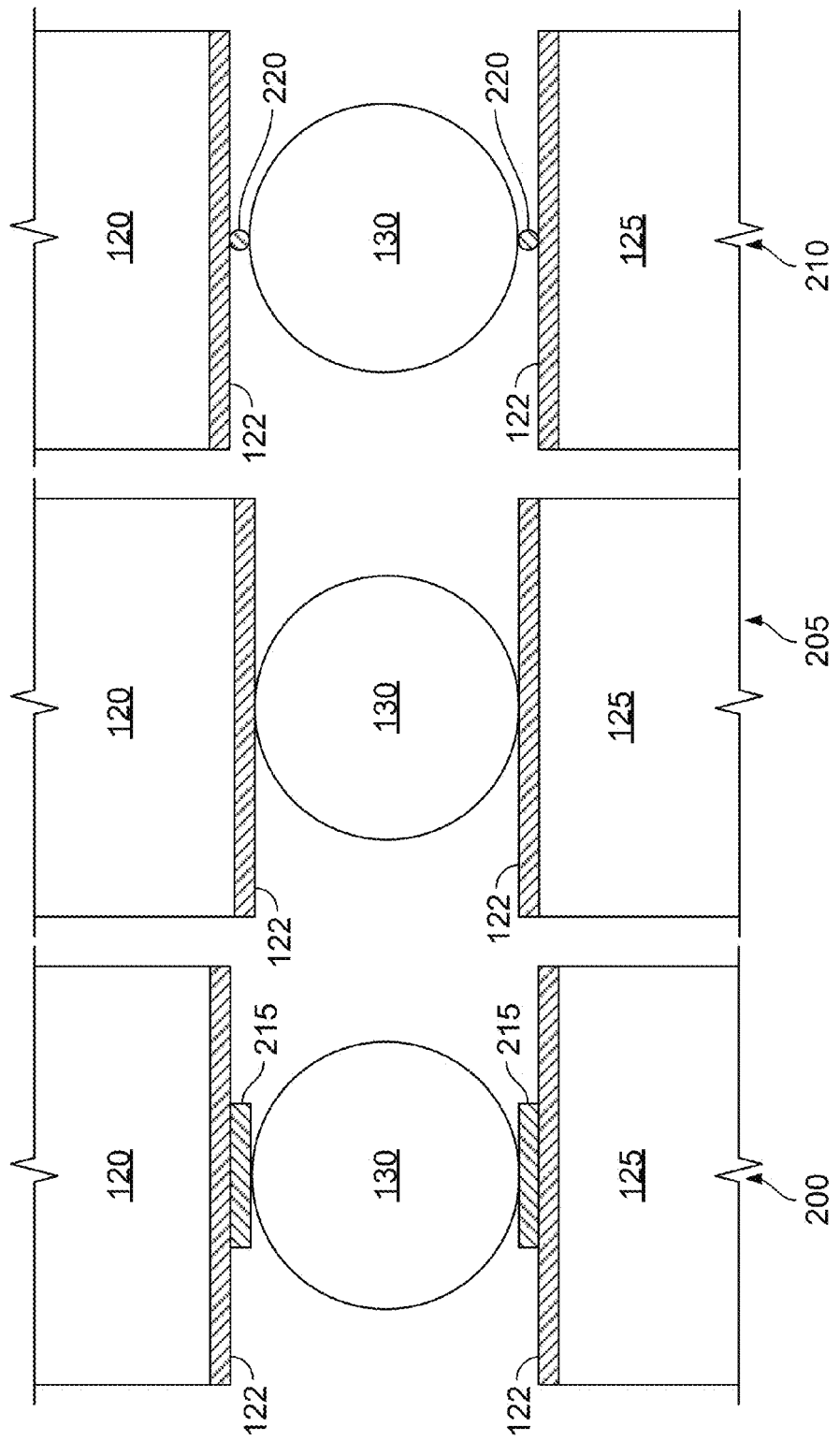
FIG. 2A-2C are schematic illustrations of several example loading assemblies of a test apparatus for determining one or more rock mechanical properties according to the present disclosure.

Turning briefly to FIGS. 2A-2C, schematic illustrations of several example loading assemblies of the test apparatus 100 are illustrated. As shown, each platen (upper platen 120 and lower platen 125) includes a substantially planar or flat contact surface 122 to hold the rock sample 130 in between. Example loading assembly 200 in FIG. 2A includes separators 215 that are positioned between the contact surfaces 122 and the radial surface of the rock sample 130. The separators 215 may be rigid or pliable, such as cushions. During operation of the testing apparatus 100, a compressive load is transferred from the platens 120 and 125, through the separators 215, and to the rock sample 130.

Example loading assembly 205 in FIG. 2B includes no barriers between the contact surfaces 122 and the radial surface of the rock sample 130. Thus, during operation of the test apparatus 100, a compressive load is transferred from the platens 120 and 125 directly to the rock sample 130.

Example loading assembly 210 in FIG. 2C includes a rod 220 (for example, a steel or other rigid rod) is positioned between each contact surface 122 and the radial surface of the rock sample 130. During operation of the testing apparatus 100, a compressive load is transferred from the platens 120 and 125, through the rods 220, and to the rock sample 130.

Figure 3:
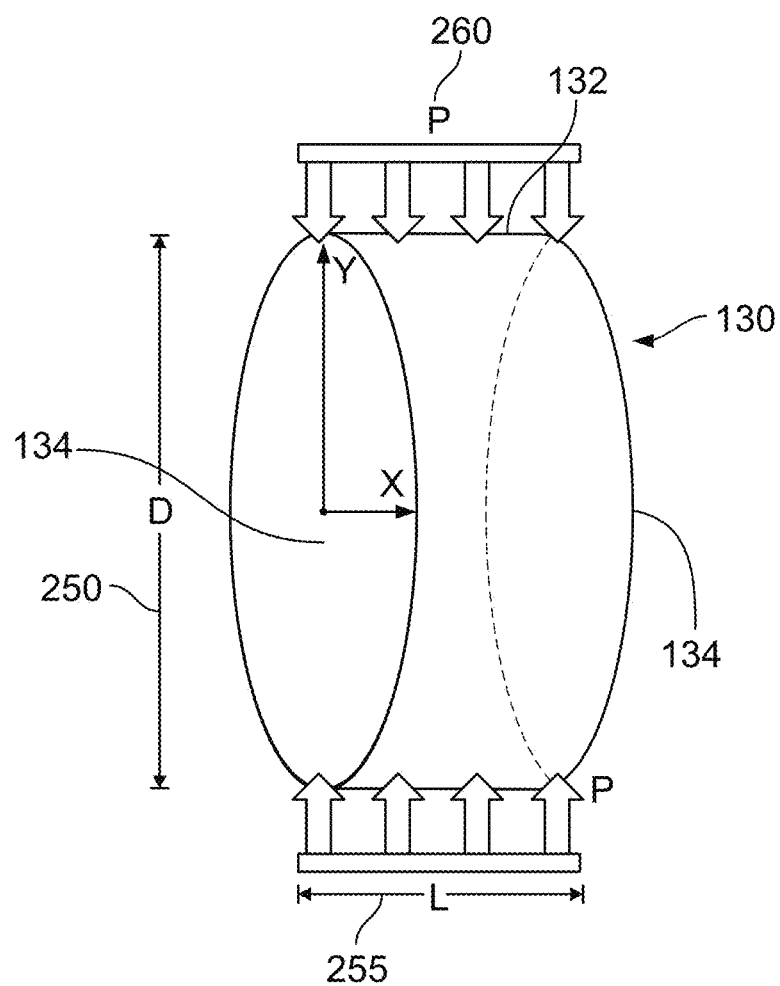
FIG. 3 is a schematic illustration of a rock sample according to the present disclosure.

FIG. 3 is a schematic illustration of the rock sample 130. As shown, the rock sample 130 has a diameter 250 of "D" and a length 255 of "L." A ratio of length-to-diameter of the rock sample 130 may vary; thus, the rock sample 130 may have various sizes, as appropriate, for example, based on the testing apparatus 100. In some aspects, the rock sample 130 may have a specified length-to-diameter ratio that conforms with the American Society for Testing and Materials (ASTM) Standard D3967-08: "Standard Test Method for Splitting Tensile Strength of Intact Rock Core Specimens." Under this Standard, for example, a diameter of the rock sample 130 must be at least 10 times greater than the largest mineral grain constituent. In some implementations, therefore, a length-to-diameter ratio of the rock sample 130 confirming to this Standard is between 0.2 and 0.75.

As shown in FIG. 3, the rock sample 130 has a radial surface 132 and two opposed axial surfaces 134. During operation of the testing apparatus 100, a compressive load 260 (labeled "P" in this figure) is exerted on the radial surface 132 of the rock sample, through the platens 120 and 125 (which are shown in FIG. 1 and FIGS. 2A-2C).

Figure 4B:
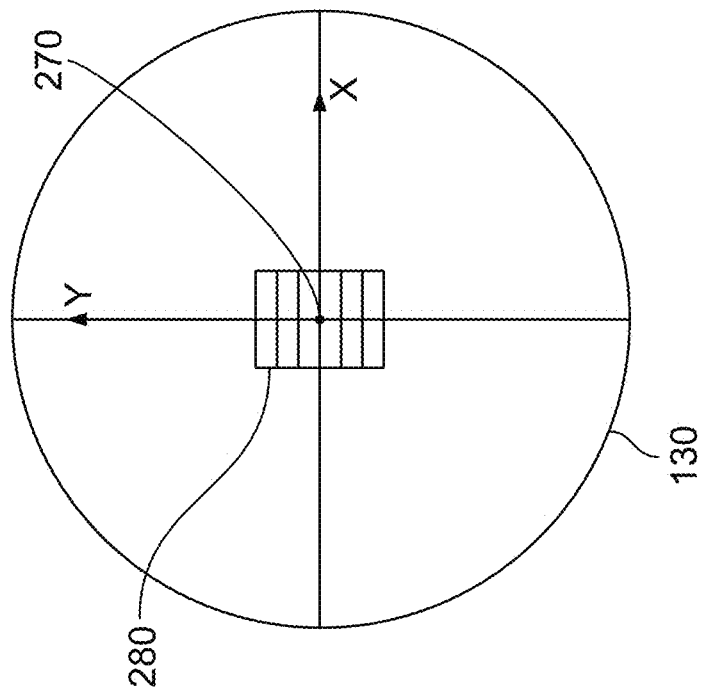
FIGS. 4A-4B are schematic illustrations of a rock sample that include at least one strain gauge according to the present disclosure.
Figure 4A:
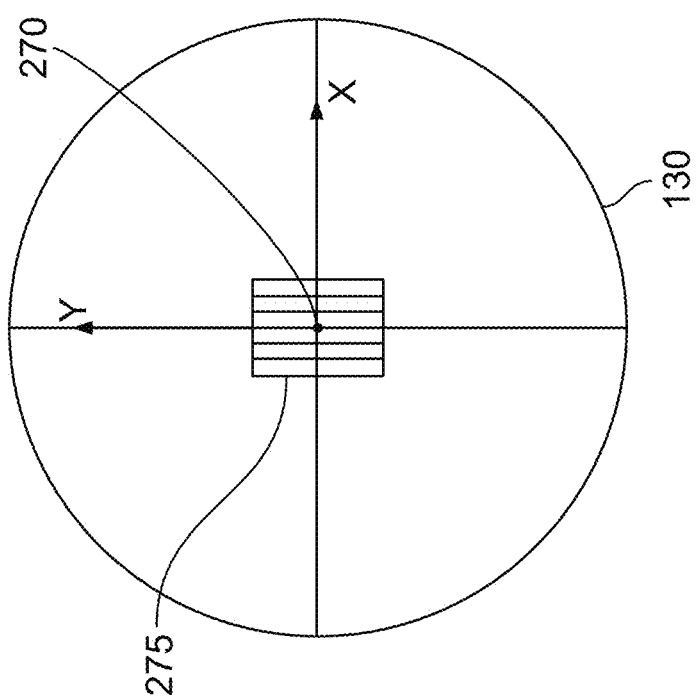

FIGS. 4A-4B are schematic illustrations of the rock sample 130 that includes at least one strain gauge. In FIG. 4A, a strain gauge 275 is attached (for example, with adhesive) to the rock sample 130 at a center point 270 of an axial face of the sample 130. The strain gauge 275, in FIG. 4A, may be an axial strain gauge that measures an axial strain (for example, strain along an x-axis, as shown in FIG. 3) during compressive loading of the rock sample 130. In FIG. 4B, a strain gauge 280 is attached (for example, with adhesive) to the rock sample 130 at the center point 270 of the axial face of the sample 130. The strain gauge 280, in FIG. 4B, may be a radial strain gauge that measures a radial strain (for example, strain along a y-axis, as shown in FIG. 3) during compressive loading of the rock sample 130. Although each strain gauge 275 and 280 is illustrated as attached independently to the rock sample 130, in some implementations, the two strain gauges (275 and 280) are both attached to the rock sample 130, so that both axial and radial strain on the rock sample 130 may be measured during compressive loading (for example, during a Brazilian test of the rock sample 130 using the testing apparatus 100).

Thus, during an example operation of the testing apparatus 130, the compressive load, P, is known, as is the diameter, D, and length, L, of the rock sample 130. Also known is an effective length, 2l of the strain gauges 275 and 280 (which, in some implementations, is identical). In the example operation, P is measured in Newtons (N), and D, L, and 2l are measured in millimeters (mm). Thus, for rock sample 130 (for example, an isotropic or anisotropic sample), the stress state for the sample 130 may be determined according to Equations (1) to (3):

$$\sigma_x = \frac{2P}{\pi L}\left\{\frac{\left(\left(\frac{D}{2}\right)-y\right)x^2}{\left(\left(\left(\frac{D}{2}\right)-y\right)^2+x^2\right)^2} + \frac{\left(\left(\frac{D}{2}\right)+y\right)x^2}{\left(\left(\left(\frac{D}{2}\right)+y\right)^2+x^2\right)^2} - \frac{1}{D}\right\} \quad \text{Eq. 1}$$

$$\sigma_y = \frac{2P}{\pi L}\left\{\frac{\left(\left(\frac{D}{2}\right)-y\right)^3}{\left(\left(\left(\frac{D}{2}\right)-y\right)^2+x^2\right)^2} + \frac{\left(\left(\frac{D}{2}\right)+y\right)^3}{\left(\left(\left(\frac{D}{2}\right)+y\right)^2+x^2\right)^2} - \frac{1}{D}\right\} \quad \text{Eq. 2}$$

$$\tau_{xy} = \frac{2P}{\pi L}\left\{\frac{\left(\left(\frac{D}{2}\right)-y\right)^2 x}{\left(\left(\left(\frac{D}{2}\right)-y\right)^2+x^2\right)^2} + \frac{\left(\left(\frac{D}{2}\right)+y\right)^2 x}{\left(\left(\left(\frac{D}{2}\right)+y\right)^2+x^2\right)^2}\right\} \quad \text{Eq. 3}$$

In Equations (1) to (3), $\sigma_x$ is a normal stress along the x-axis of the rock sample 130 (as shown in FIG. 3), $\sigma_y$ is a normal stress along the y-axis of the rock sample 130 (as shown in FIG. 2B), and $\tau_{xy}$ is a shear stress. Each stress has units of mega Pascals (MPa).

Because the effective length of the strain gauges 275 and 280 is known, as well as the diameter of the rock sample 130, two constant coefficients, A and B, may be developed based on the geometry of the strain gauges 275 and 280, according to Equations (4) and (5):

$$A = \left(\frac{D}{2} - l\right) \quad \text{Eq. 4}$$

$$B = \left(\frac{D}{2} + l\right) \quad \text{Eq. 5}$$

Based on Equations (1) to (5), the following equations for an average value of the normal stress, $\overline{\sigma}_x$ (along a side boundary of strain gauge 275) and $\overline{\sigma}_y$ (along a top boundary of the strain gauge 280) can be expressed as:

$$\overline{\sigma}_x = \frac{1}{l}\int_0^l \frac{2P}{\pi L}\left[\frac{\left(\left(\frac{D}{2}\right)-y\right)l^2}{\left(\left(\left(\frac{D}{2}\right)-y\right)+l^2\right)^2} + \frac{\left(\left(\frac{D}{2}\right)+y\right)l^2}{\left(\left(\left(\frac{D}{2}\right)+y\right)+l^2\right)^2} - \frac{1}{D}\right]dy \quad \text{Eq. 6}$$

$$\overline{\sigma}_y = \frac{1}{l}\int_0^l \frac{2P}{\pi L}\left[\frac{A^3}{(A^2+x^2)^2} + \frac{B^3}{(B^2+x^2)^2} - \frac{1}{D}\right]dx \quad \text{Eq. 7}$$

Equations (6) and (7) can then be integrated to produce the following equations for the average values of the normal stress, $\overline{\sigma}_x$ and $\overline{\sigma}_y$.

$$\overline{\sigma}_x = \frac{P}{l\pi L}\left[l^2\left(\frac{1}{A^2+l^2} - \frac{1}{B^2+l^2}\right) - \frac{2l}{D}\right] \quad \text{Eq. 8}$$

$$\overline{\sigma}_y = \frac{2P}{l\pi L}\left\{\frac{A^3}{2}\left[\frac{1}{A^3}\arctan\frac{l}{A} + \frac{l}{A^2(l^2+A^2)}\right] + \frac{B^3}{2}\left[\frac{1}{B^3}\arctan\frac{l}{B} + \frac{l}{B^2(l^2+B^2)}\right] - \frac{l}{D}\right\} \quad \text{Eq. 9}$$

Based on Equations (8) and (9), two coefficients may be developed based on the strain gauge and rock sample geometry (for example, effective length of the strain gauges 275/280 and diameter and length of the rock sample 130). These coefficients, F and G, may be expressed according to Equations (10) and (11):

$$F = \frac{1}{l\pi L}\left(l^2\left(\frac{1}{A^2+l^2} - \frac{1}{B^2+l^2}\right) - \frac{2l}{D}\right) \quad \text{Eq. 10}$$

$$G = \frac{1}{l\pi L}\left\{A^3\left[\frac{1}{A^3}\arctan\frac{l}{A} + \frac{l}{A^2(l^2+A^2)}\right] + B^3\left[\frac{1}{B^3}\arctan\frac{l}{B} + \frac{l}{B^2(l^2+B^2)}\right] - \frac{2l}{D}\right\} \quad \text{Eq. 11}$$

Thus, both F and G are constant coefficients related to D, L and 2l, and Equations (8) and (9) can be simplified as:

$$\overline{\sigma}_x = PF \quad \text{Eq. 12}$$

$$\overline{\sigma}_y = PG \quad \text{Eq. 13}$$

According to the relationship of strain and stress, the tensile strain ($\epsilon_x$) and compressive strain ($\epsilon_y$) on the rock sample 130 during compressive loading is generated by both $\overline{\sigma}_x$ and $\overline{\sigma}_y$ according to the following Equations (14) and (15):

$$\varepsilon_x = \frac{1}{E}(-\overline{\sigma}_x + \upsilon\overline{\sigma}_y) \quad \text{Eq. 14}$$

$$\varepsilon_y = \frac{1}{E}(-\upsilon\overline{\sigma}_x + \overline{\sigma}_y) \quad \text{Eq. 15}$$

In Equations (14) and (15), $\epsilon_x$ is the tensile, or radial, strain, $\epsilon_y$ is the compressive, or axial, strain, E is the tensile elastic modulus, and υ is Poisson's ratio. By substituting Equations (12) and (13) into Equations (14) and (15), Equations (16) and (17) follow:

$$\varepsilon_x = \frac{P}{E}(-F + \upsilon G) \quad \text{Eq. 16}$$

$$\varepsilon_y = \frac{P}{E}(-\upsilon F + G) \quad \text{Eq. 17}$$

Therefore, the radial strain and axial strain are the function of tensile elastic modulus (Young's modulus) and Poisson's ratio of the rock sample 130. According to Equations (16) and (17), Poisson's ratio is calculated as:

$$\upsilon = \frac{\left(\frac{\varepsilon_x}{\varepsilon_y}\right)G + F}{\left(\frac{\varepsilon_x}{\varepsilon_y}\right)F + G} \quad \text{Eq. 18}$$

By exchanging $\epsilon_x$ and E in Equation (16), the tensile elastic modulus (Young's modulus) can be formulated as:

$$E = \frac{P}{\varepsilon_x}(-F + \upsilon G) \quad \text{Eq. 19}$$

Therefore, according to Equations (18) and (19), the radial strain and axial strain are functions of elastic mechanical properties of the rock sample 130: the tensile elastic modulus (Young's modulus) and Poisson's ratio. During operation of the testing apparatus 100 in exerting a compressive load on the rock sample 130, the radial and axial strains are measured by the strain gauges 280 and 275, respectively. Thus, for a known incremental compressive load exerted on the rock sample 130 by the testing apparatus 100, the elastic properties of tensile elastic modulus (Young's modulus) and Poisson's ratio can be determined, for example, by the control system 140. When the Young's modulus and Poisson's ratio for the rock sample 130 are stress dependent, implementations of the present disclosure allow for determining the related parameters based on the superposition principle. Since the elastic properties are obtained from the linear section of stress-strain curve, the Young's modulus and Poisson's ratio can also be written as Equations (20) and (21):

$$E = \frac{\Delta P}{\Delta \varepsilon_x}(-F + \upsilon G) \quad \text{Eq. 20}$$

$$\upsilon = \frac{\left(\frac{\Delta\varepsilon_x}{\Delta\varepsilon_y}\right)G + F}{\left(\frac{\Delta\varepsilon_x}{\Delta\varepsilon_y}\right)F + G} \quad \text{Eq. 21}$$

Therefore, during operation of the testing apparatus 100 to test the rock sample 130, both mechanical and elastic properties of the rock sample 130 can be determined with a single test (for example, a single Brazilian test). For example, as outlined previously, the elastic properties of Young's modulus and Poisson's ratio for each loading (P) under which strain increments are measured (by strain gauges 275 and 280) can be determined for the rock sample 130. Also, the corresponding stresses can be obtained from Equations (12) and (13) for a given loading, P.

Other mechanical properties, such as tensile strength, of the rock sample 130 may also be determined during the test. For instance, tensile strength, $\sigma_t$, can be determined at failure of the rock sample 130 (at a particular load, P) according to:

$$\sigma_t = \frac{2P}{\pi DL} \quad \text{Eq. 22}$$

Accordingly, an example operation with the testing apparatus includes preparing the rock sample 130 for testing, for example, according to ASTM D3967-08 with a length-to-diameter ration of between 0.2 and 0.75. The strain gauges 275 and 280 are attached to the rock sample 130, which is placed within the testing apparatus between the upper and lower platens 120 and 125, respectively. A compression test (for example, a Brazilian test) is conducted with the testing apparatus 100, and the incremental compressive loads (ΔP), along with resulting axial and radial strains, on the rock sample 130 are recorded (for example, by the control system 140). Based on the known geometries of the rock sample 130 (for example, D and L) and the known geometry of the strain gauges 275 and 280 (for example, l), the aforementioned mechanical properties may be determined. Mechanical properties of the rock sample 130, such as tensile strength, may be calculated, as well as elastic properties, such as Young's modulus and Poisson's ratio.

Figure 5:
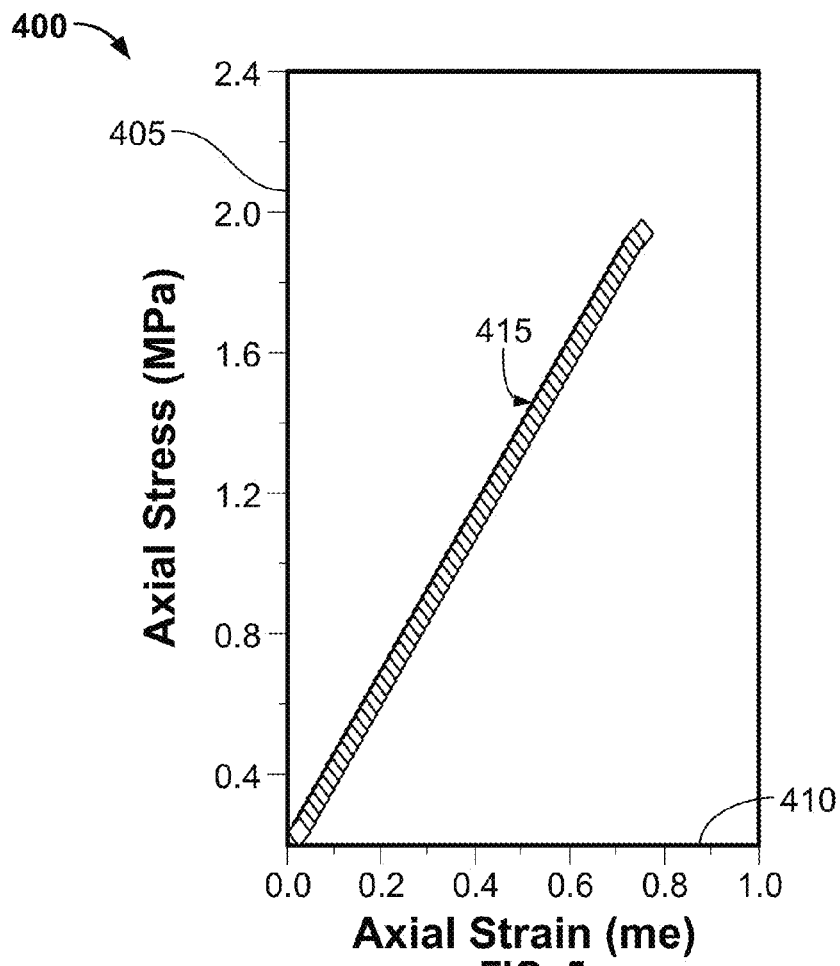
FIG. 5 is a graph that illustrates Young's modulus of a rock sample during testing according to the present disclosure.

FIG. 5 is a graph 400 that illustrates a determination of Young's modulus (E) of a rock sample during testing. For example, graph 400 illustrates the results of testing on one of six rock samples according to the operation of testing apparatus 100 described in this disclosure. The rock samples are shale, each with dimensions of about 25.4 mm diameter and 19.1 mm length (providing a length-to-diameter ratio of about 0.75). Graph 400 illustrates the results of one of the six tested samples, and includes a y-axis 405 for axial stress (in units of MPa) of the rock sample and an x-axis 410 of the axial strain (in units of millistrain (me)) of the rock sample during compressive loading increments. Because Young's modulus is determined by a slope of a stress-strain curve 415 over the incremental compressive loading, graph 400 shows this slope to be about 3.0 GPa.

Figure 6:
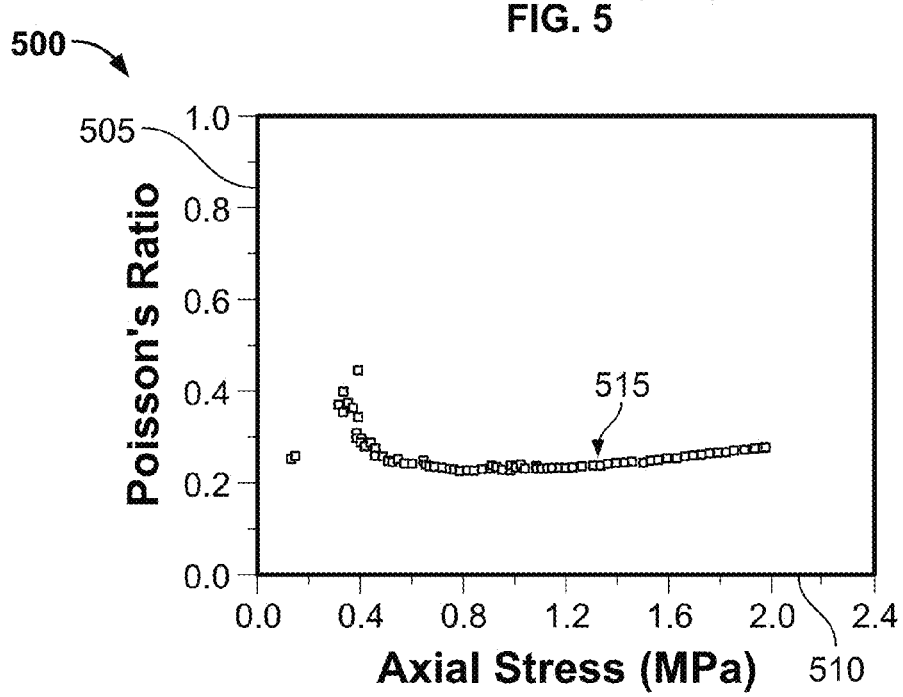
FIG. 6 is a graph that illustrates stress-strain curve and Poisson's ratio of a rock sample during testing according to the present disclosure.

FIG. 6 is a graph 500 that illustrates a determination of Poisson's ratio (u) of a rock sample during testing based on Eq. 21. For a given stress condition (or a given P), measured increments of strains during a compressive load increment are used to calculate Young's modulus (E) and Poisson's ratio (υ). In this way, Young's modulus (E) and Poisson's ratio (υ) are determined as functions of stress. As with graph 400, graph 500 illustrates the results of testing on one of six rock samples according to the operation of testing apparatus 100 described in this disclosure. The rock samples are shale, each with dimensions of about 25.4 mm diameter and 19.1 mm length (providing a length-to-diameter ratio of about 0.75). Graph 500 illustrates the results of one of the six tested samples, and includes a y-axis 505 for Poisson's ratio of the rock sample and an x-axis 510 of the axial stress of the rock sample during compressive loading increments. As illustrated, except for some initial loading increments, the Poisson's ratio plot 515 of the tested sample is between about 0.2 and 0.3.

Figure 7:
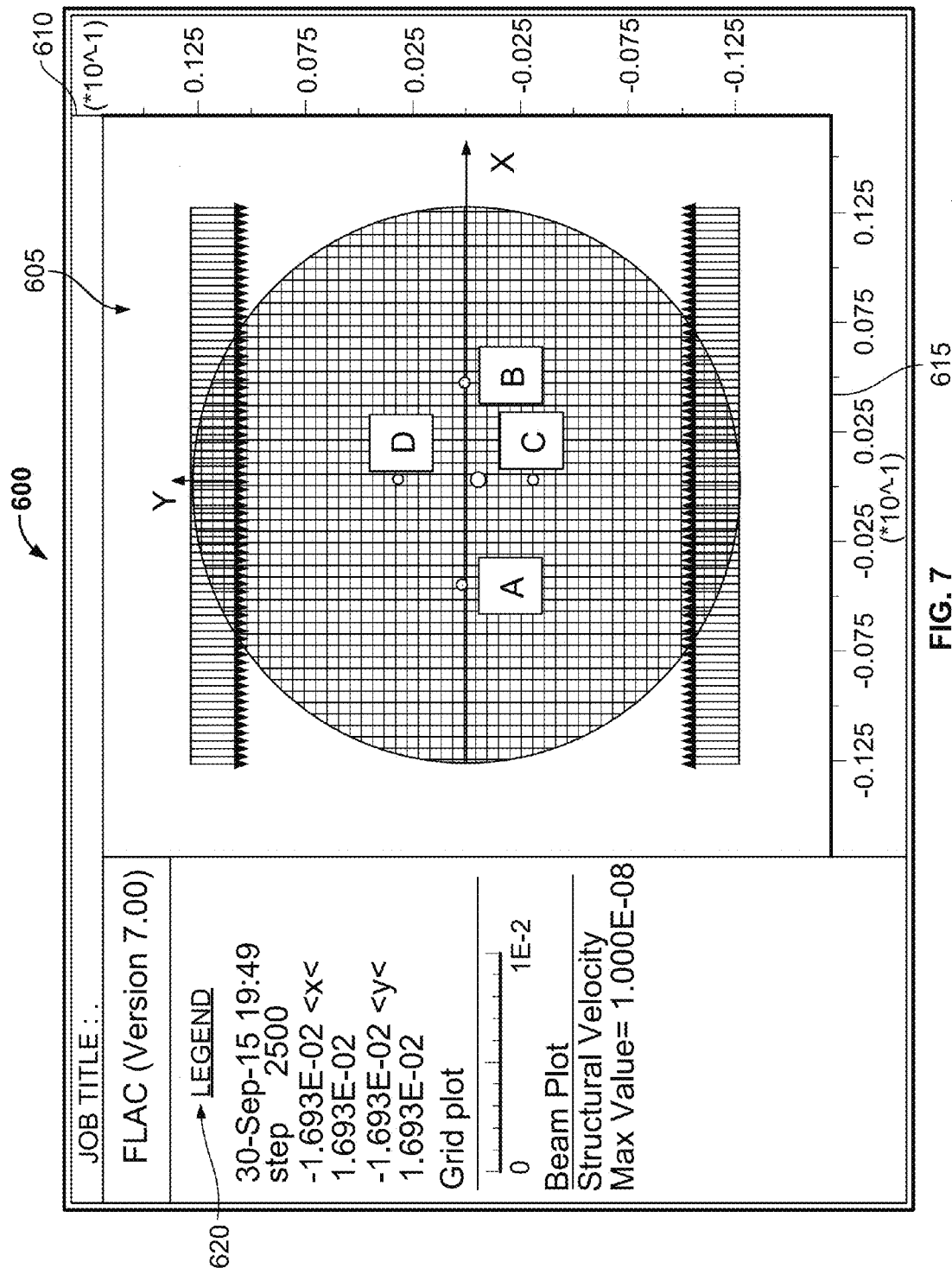
FIG. 7 is a numerical model of a rock sample that is determined during a rock sample test simulation according to the present disclosure.

FIG. 7 is a graph 600 of a numerical model 605 of a rock sample that is determined during a rock sample test simulation. For example, to further confirm the previously described operation of the testing apparatus 100 to perform a single test on a rock sample to determine elastic and mechanical properties, a numerical model was developed in FLAC®. The numerically modeled rock sample comprises a disc having a diameter of about 25.4 mm. In the legend 620 of FIG. 6, "Grid Plot" presents the computational mesh for simulating Brazilian disc test in a FLAC® numerical model; "Beam Plot" indicates the loading platens; "Structure Velocity" shows that the Brazilian disc is loaded by two platens at a constant loading rate in the model.

In the model 605, the rock sample is loaded by two platens, one at the top and the other at the bottom, in strain control mode. The simulation is stopped after the rock sample is squeezed for 0.2 mm in the vertical (axial) direction. The load, P, applied on the platens is measured as 215 KN. The contour of the vertical stress distribution inside the disc given by the numerical model 605, which compares well with the analytical solution in Eq. (2). In these plots, the numerical solutions are computed from FLAC® simulation; while the analytical solutions are obtained by programming closed-form solution Eq. (2) into functions using FISH®, a built-in programming language in FLAC®. This function is executed at the center of all zones in the FLAC® numerical model 605 so that direct comparison can be made between the numerical solutions shown in FIG. 7 and analytical solutions using the previously-described equations. As shown in FIG. 7, the numerical solution and analytical solution of vertical stress are substantially identical.

The strains developed along the strain gauges attached to the rock sample in the model 605 can be calculated from measurement of two symmetric points along the x-axis and the y-axis in the model 650, for example, the strains between 'A'-'B' and 'C'-'D.' As shown in the graph 600, an axial strain is measured by axis 610 while a radial strain is measured by axis 615 (both axes have units of mm). The aforementioned strains 'A'-'B' and 'C'-'D' are determined as follows:

$$\varepsilon_{lx} = \frac{x_d^B - x_d^A}{x^B - x^A}$$ Eq. 23

$$\varepsilon_{ly} = \frac{y_d^D - y_d^C}{y^D - y^C}$$ Eq. 24

In Eqs. (23) and (24), $x_d^A$ and $x_d^B$ are the x-displacement at points A and B (shown in FIG. 7) which are symmetric about the origin, and $x^A$ and $x^B$ are the x-coordinates at A and B (note, both points are on the x-axis, so y=0). Similarly, $y_d^C$ and $y_d^D$ are the y-displacement at points C and D (shown in FIG. 7) which are symmetric about the origin, and $y^C$ and $y^D$ are the y-coordinates at C and D (note, both points are on the y-axis, so x=0).

The Young's modulus and Poisson's ratio can be calculated from the applied load on the platens and the measured strains (for example, $\epsilon_{lx}$ and $\epsilon_{ly}$). For short strain gauges (for example, their length is only 1% of disc diameter), the calculated Young's modulus is 8.18 GPa and Poisson's ratio is 0.364.

Figure 8:
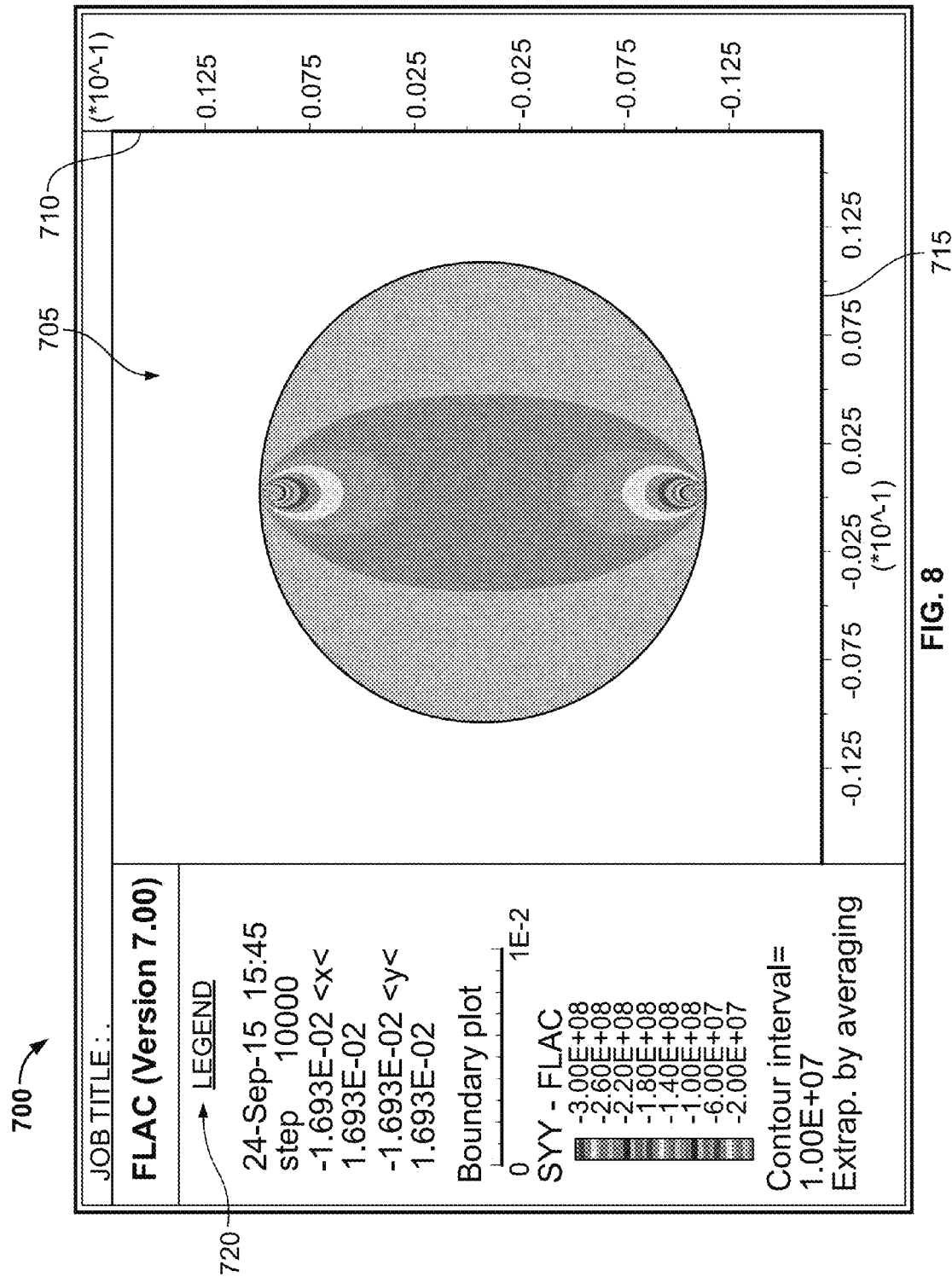
FIGS. 8 and 9 are numerical models of vertical and horizontal stress contours, respectively, of a rock sample that are determined during a rock sample test simulation according to the present disclosure.
Figure 9:
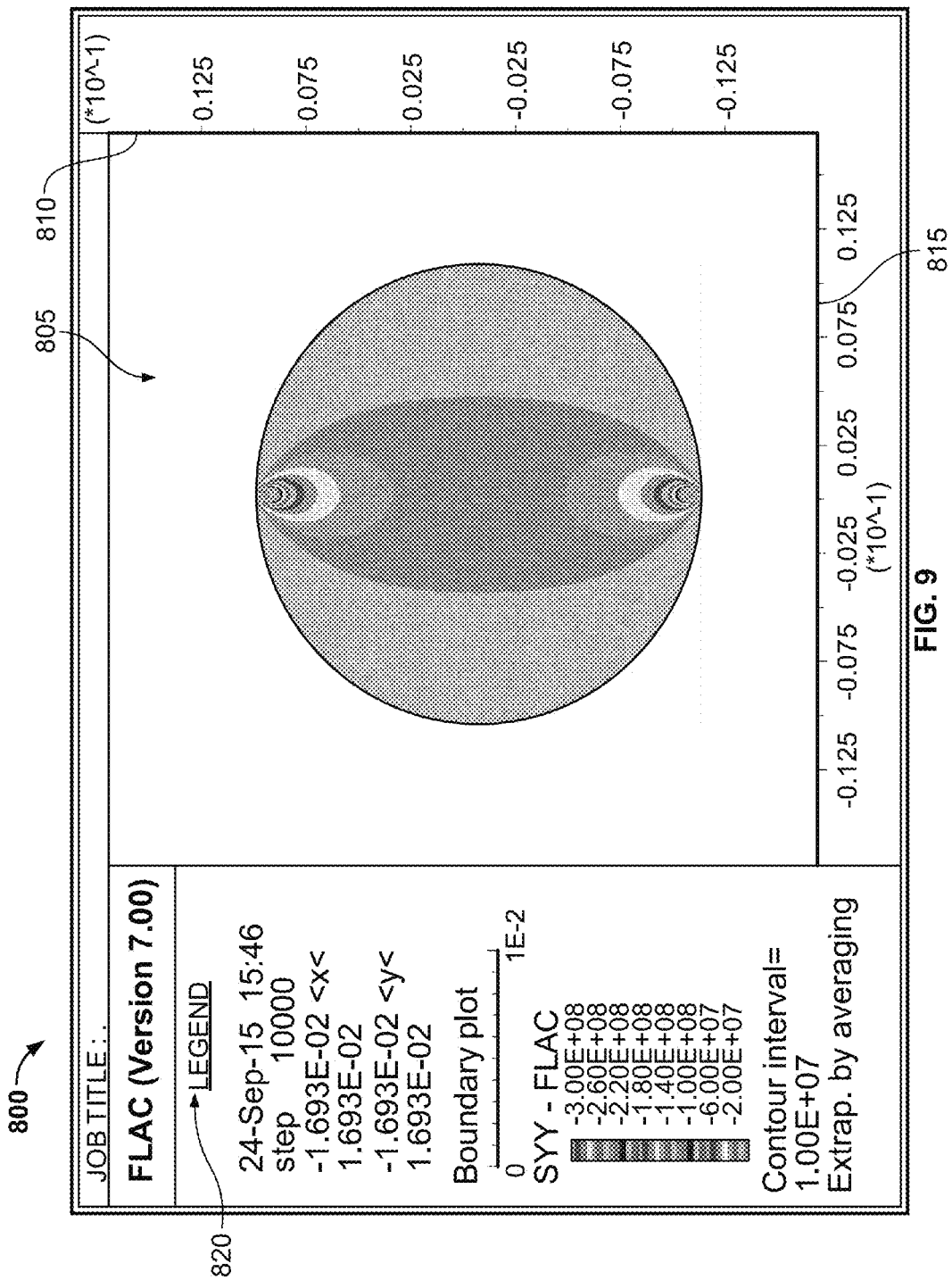

FIG. 8 illustrates a graph 700 of a numerical model 705 of vertical stress contours of the rock sample that are determined during the rock sample test FLAC® simulation as described previously. FIG. 9 illustrates a graph 800 of a numerical model 805 of horizontal stress contours of the rock sample that are determined using the analytical solution (for example, with Eq. (2)) as described previously. FIGS. 8 and 9, for example, demonstrate the stress distribution within the rock sample according to the FLAC® simulation. In FIG. 8, the graph 700 includes an x-axis 715 that shows displacement of the radial strain gauge (in mm), while a y-axis 710 shows displacement of the radial strain gauge (in mm). In the legend 720, "Boundary plot" marks the boundary of a Brazilian disc (the rock sample); "SYY-FLAC" shows the vertical stress contour resulting from the vertical load of 215 KN predicted by the numerical model in FLAC®. In FIG. 9, the graph 800 includes an x-axis 815 that shows displacement of the radial strain gauge (in mm), while a y-axis 810 shows displacement of the radial strain gauge (in mm). In the legend 820, "SYY-analytical" indicates the vertical stress contour resulting from the vertical load of 215 KN evaluated by the analytical solution (Eq. 2) described in this disclosure.

Figure 10:
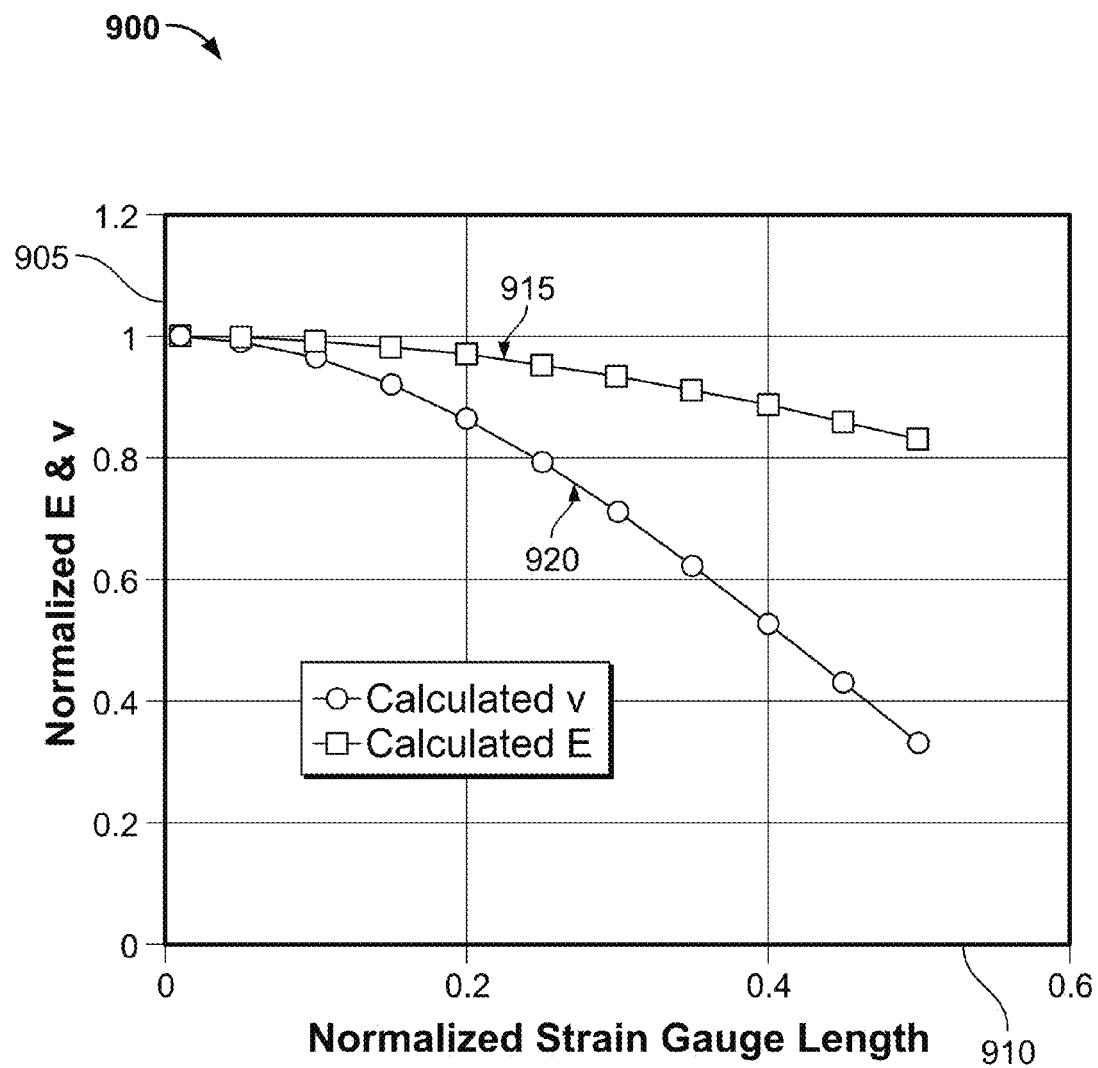
FIG. 10 is a graph that illustrates normalized Young's modulus and Poisson's ratio of a rock sample that are determined during a rock sample test simulation according to the present disclosure.

FIG. 10 is a graph 900 that illustrates normalized Young's modulus and Poisson's ratio of the rock sample that are determined during the rock sample test simulation in FLAC® described previously. Graph 900 includes an x-axis 910 that represents normalized strain gauge length (dimensionless) and a y-axis 905 that represents normalized values for Young's modulus and Poisson's ratio. Calculated Young's modulus is represented by plot 915, while calculated Poisson's ratio is represented by plot 920. As shown by plots 915 and 920, the calculated elastic properties of the simulated rock sample test may be dependent on the geometric relationship between the strain gauges used to measure axial and radial strain and the rock sample disc. For example, as the length of the strain gauges increases, the calculated Young's modulus and Poisson's ratio decrease, as shown in graph 900. Note that the Young's modulus is normalized by 8.18 GPa and Poisson's ratio normalized by 0.364 in FIG. 10. In some aspects, therefore, the measurement of Young's modulus and Poisson's ratio may be quite accurate if the strain gauge length is less than 10% of the disc diameter of the rock sample.

Figure 11:
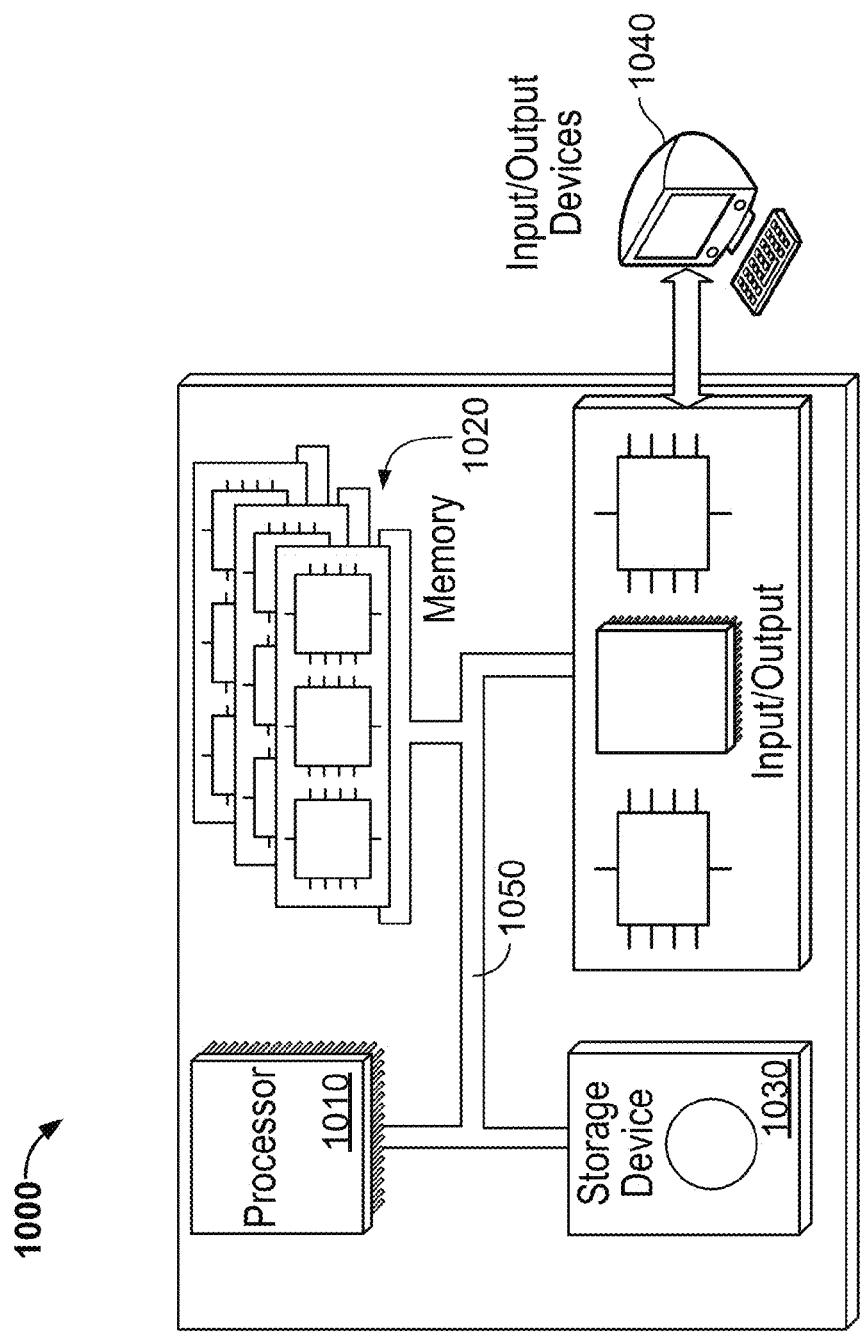
FIG. 11 is a schematic illustration of an example controller of a testing apparatus for determining one or more rock mechanical properties according to the present disclosure.

FIG. 11 is a schematic illustration of an example controller 1000 of a testing apparatus for determining one or more rock mechanical properties. For example, the controller 1000 can be used for the operations described previously, for example as or as part of the control system 140 or other controllers described in this disclosure. For example, the controller 1000 may be communicably coupled with, or as a part of, one or both of a vehicle engine and on-board fuel separation system as described in this disclosure.

The controller 1000 is intended to include various forms of digital computers, such as printed circuit boards (PCB), processors, or digital circuitry, that is part of a vehicle. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The controller 1000 includes a processor 1010, a memory 1020, a storage device 1030, and an input/output device 1040. Each of the components 1010, 1020, 1030, and 1040 are interconnected using a system bus 1050. The processor 1010 is capable of processing instructions for execution within the controller 1000. The processor may be designed using any of a number of architectures. For example, the processor 1010 may be a CISC (Complex Instruction Set Computers) processor, a RISC (Reduced Instruction Set Computer) processor, or a MISC (Minimal Instruction Set Computer) processor.

In one implementation, the processor 1010 is a single-threaded processor. In another implementation, the processor 1010 is a multi-threaded processor. The processor 1010 is capable of processing instructions stored in the memory 1020 or on the storage device 1030 to display graphical information for a user interface on the input/output device 1040.

The memory 1020 stores information within the controller 1000. In one implementation, the memory 1020 is a computer-readable medium. In one implementation, the memory 1020 is a volatile memory unit. In another implementation, the memory 1020 is a non-volatile memory unit.

The storage device 1030 is capable of providing mass storage for the controller 1000. In one implementation, the storage device 1030 is a computer-readable medium. In various different implementations, the storage device 1030 may be a floppy disk device, a hard disk device, an optical disk device, or a tape device.

The input/output device 1040 provides input/output operations for the controller 1000. In one implementation, the input/output device 1040 includes a keyboard and/or pointing device. In another implementation, the input/output device 1040 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, for example, in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semi-conductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Additionally, such activities can be implemented via touch-screen flat-panel displays and other appropriate mechanisms.

The features can be implemented in a control system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described previously as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described previously should not be understood as requiring such separation in all implementations, and it should be understood that the described program components and systems can generally be integrated together in a single software product or packaged into multiple software products.

A number of implementations have been described. Nevertheless, it will be understood that various modifications may be made without departing from the spirit and scope of the disclosure. For example, example operations, methods, or processes described in this disclosure may include more steps or fewer steps than those described. Further, the steps in such example operations, methods, or processes may be performed in different successions than that described or illustrated in the figures. Accordingly, other implementations are within the scope of the following claims.

What is claimed is:

1. A method for determining rock properties, comprising:
    exerting a compressive load with a Brazilian test apparatus across a rock sample that comprises a specified length-to-diameter ratio;
    measuring, with the Brazilian test apparatus, a tensile strength of the rock sample based on the compressive load;
    measuring, with at least one strain gauge that is coupled to an axial surface of the rock sample, a strain on the rock sample during the compressive loading, the measuring comprising:
        measuring an incremental axial strain on the rock sample during a compressive load increment with a first strain gauge, and
        measuring an incremental radial strain on the rock sample during the compressive load increment with a second strain gauge;
    determining, based at least in part on the compressive load, a mechanical property of the rock sample; and
    determining, based at least in part on the measured strain and the compressive load, an elastic property of the rock sample, the determining comprising:
        determining a first coefficient based at least in part on the diameter of the rock sample, the length of the rock sample, and an effective length of the first and second strain gauges,
        determining a second coefficient based at least in part on the diameter of the rock sample, the length of the rock sample, and the effective length of the first and second strain gauges, and
        determining the elastic property of the rock sample based at least in part on the measured incremental axial and radial strains on the rock sample, the first and second coefficients, and the compressive loading increment.

2. The method of claim 1, wherein the specified length-to-diameter ratio is between 0.2 and 0.75.

3. The method of claim 1, wherein determining, based at least in part on the measured strain and the compressive load, the elastic property of the rock sample comprises determining a Young's modulus of the rock sample based on at least one of:

$$E = \frac{\Delta P}{\Delta \varepsilon_x}(-F + vG), \quad \text{(i)}$$

where E is stress dependent Young's modulus of the rock sample, $\Delta P$ is the compressive loading increment, $\Delta \epsilon_x$ is the incremental radial strain, $\upsilon$ is Poisson's ratio of the rock sample, F is a first coefficient, and G is a second coefficient; or $$E = \frac{P}{\varepsilon_x}(-F + vG), \quad \text{(ii)}$$

where E is Young's modulus of the rock sample, P is a particular compressive load, $\epsilon_x$ is a radial strain at the particular compressive load, $\upsilon$ is Poisson's ratio of the rock sample, F is the first coefficient, and G is the second coefficient.

4. The method of claim 1, wherein determining, based at least in part on the measured strain and the compressive load, the elastic property of the rock sample comprises determining Poisson's ratio of the rock sample based on at least one of:

$$\upsilon = \frac{\left(\frac{\Delta \varepsilon_x}{\Delta \varepsilon_y}\right)G + F}{\left(\frac{\Delta \varepsilon_x}{\Delta \varepsilon_y}\right)F + G}, \quad \text{(i)}$$

where $\upsilon$ is stress dependent Poisson's ratio of the rock sample, $\Delta \epsilon_x$ is the incremental radial strain, $\Delta \epsilon_y$ is the incremental axial strain, F is a first coefficient, and G is a second coefficient; or $$\upsilon = \frac{\left(\frac{\varepsilon_x}{\varepsilon_y}\right)G + F}{\left(\frac{\varepsilon_x}{\varepsilon_y}\right)F + G}, \quad \text{(ii)}$$

where $\upsilon$ is Poisson's ratio of the rock sample, $\epsilon_x$ is a radial strain at a particular compressive load on the rock sample, $\Delta\epsilon_y$ is an axial strain at the particular compressive load on the rock sample, F is the first coefficient, and G is the second coefficient.

5. The method of claim 1, wherein the mechanical property comprises at least one of a tensile strength or a brittleness of the rock sample.

6. The method of claim 1, wherein the strain gauge comprises a linear variable differential transformer (LVDT).

7. A rock property test system, comprising:
   a load cell configured to exert a compressive load across a rock sample, the load cell comprising a Brazilian test apparatus;
   at least one strain gauge configured to attach to an axial surface of the rock sample and positioned to measure a strain on the rock sample during the compressive loading, the at least one strain gauge comprising a first strain gauge configured to measure an incremental axial strain on the rock sample during the incremental compressive load and a second strain gauge configured to measure an incremental radial strain on the rock sample during the incremental compressive load; and
   a control system communicably coupled to the load cell and the at least one strain gauge and configured to perform operations comprising:
      controlling the load cell to exert an incremental compressive load on the rock sample;
      determining a tensile strength of the rock sample based on the compressive load;
      receiving a measured incremental axial strain on the rock sample and a measured incremental radial strain on the rock sample, based on the incremental compressive load, from the at least one strain gauge;
      determining a first coefficient based at least in part on the diameter of the rock sample, the length of the rock sample, and an effective length of the first and second strain gauges;
      determining a second coefficient based at least in part on the diameter of the rock sample, the length of the rock sample, and the effective length of the first and second strain gauges;
      determining, based at least in part on the incremental compressive load, a mechanical property of the rock sample; and
      determining, based at least in part on the measured incremental axial and radial strains on the rock sample, the first and second coefficients, and the incremental compressive load, an elastic property of the rock sample.

8. The rock property test system of claim 7, wherein the rock sample comprises a length-to-diameter ratio between 0.2 and 0.75.

9. The rock property test system of claim 7, wherein the operation of determining, based at least in part on the measured strain and the compressive load, the elastic property of the rock sample comprises determining a Young's modulus of the rock sample based on at least one of:

$$E = \frac{\Delta P}{\Delta\varepsilon_x}(-F + \nu G), \quad \text{(i)}$$

where E is stress dependent Young's modulus of the rock sample, $\Delta P$ is the compressive loading increment, $\Delta\epsilon_x$ is the incremental radial strain, $\upsilon$ is Poisson's ratio of the rock sample, F is a first coefficient, and G is a second coefficient; or $$E = \frac{P}{\varepsilon_x}(-F + \nu G), \quad \text{(ii)}$$

where E is Young's modulus of the rock sample, P is a particular compressive load, $\epsilon_x$ is a radial strain at the particular compressive load, $\upsilon$ is Poisson's ratio of the rock sample, F is the first coefficient, and G is the second coefficient.

10. The rock property test system of claim 7, wherein the operation of determining, based at least in part on the measured strain and the compressive load, the elastic property of the rock sample comprises determining Poisson's ratio of the rock sample based on at least one of:

$$\upsilon = \frac{\left(\frac{\Delta\varepsilon_x}{\Delta\varepsilon_y}\right)G + F}{\left(\frac{\Delta\varepsilon_x}{\Delta\varepsilon_y}\right)F + G}, \quad \text{(i)}$$

where $\upsilon$ is stress dependent Poisson's ratio of the rock sample, $\Delta\epsilon_x$ is the incremental radial strain, $\Delta\epsilon_y$ is the incremental axial strain, F is a first coefficient, and G is a second coefficient; or $$\upsilon = \frac{\left(\frac{\varepsilon_x}{\varepsilon_y}\right)G + F}{\left(\frac{\varepsilon_x}{\varepsilon_y}\right)F + G}, \quad \text{(ii)}$$

where $\upsilon$ is Poisson's ratio of the rock sample, $\epsilon_x$ is a radial strain at a particular compressive load on the rock sample, $\Delta\epsilon_y$ is an axial strain at the particular compressive load on the rock sample, F is the first coefficient, and G is the second coefficient.

11. The rock property test system of claim 7, wherein the mechanical property comprises at least one of a tensile strength or a brittleness of the rock sample.

12. A method, comprising:
    performing a Brazilian test on a rock sample, the Brazilian test comprising:
       exerting an incremental compressive load across a rock sample; and
       determining, based at least in part on the incremental compressive load, a-tensile strength of the rock sample;
    measuring, with a strain gauge, a strain on the rock sample during the incremental compressive load, the strain comprising an axial strain and a radial strain; and
    determining, based at least in part on the measured axial and radial strains on the rock sample and the incremental compressive load, an elastic property of the rock sample.

13. The method of claim 12, wherein the rock sample comprises a disc having a length-to-diameter ratio between 0.2 and 0.75.

14. The method of claim 12, wherein determining the elastic property of the rock sample based at least in part on the axial and radial strains on the rock sample and the incremental compressive load comprises:
    determining the elastic property of the rock sample based at least in part on the axial and radial strains on the rock sample, the incremental compressive load, and two predetermined constants.

15. The method of claim 14, wherein the two predetermined constants are based at least in part on a diameter of the rock sample, a length of the rock sample, and an effective length of the strain gauge.

16. A method for determining rock properties, comprising:
exerting a compressive load with a test apparatus across a rock sample that comprises a specified length-to-diameter ratio;
measuring, with at least one strain gauge, a strain on the rock sample during the compressive loading, the at least one strain gauge coupled to an axial surface of the rock sample, the measuring comprising:
measuring an incremental axial strain on the rock sample during a compressive load increment with a first strain gauge; and
measuring an incremental radial strain on the rock sample during the compressive load increment with a second strain gauge;
determining, based at least in part on the compressive load, a mechanical property of the rock sample; and
determining, based at least in part on the measured strain and the compressive load, an elastic property of the rock sample, the determining comprising:
determining a first coefficient based at least in part on the diameter of the rock sample, the length of the rock sample, and an effective length of the first and second strain gauges;
determining a second coefficient based at least in part on the diameter of the rock sample, the length of the rock sample, and the effective length of the first and second strain gauges; and
determining the elastic property of the rock sample based at least in part on the measured incremental axial and radial strains on the rock sample, the first and second coefficients, and the compressive loading increment.

17. The method of claim 16, wherein the specified length-to-diameter ratio is between 0.2 and 0.75.

18. The method of claim 16, wherein the test apparatus comprises a Brazilian test apparatus.

19. The method of claim 16, wherein the strain gauge is coupled to an axial surface of the rock sample.

20. The method of claim 16, wherein the mechanical property comprises at least one of a tensile strength or a brittleness of the rock sample.

21. The method of claim 16, wherein the strain gauge comprises a linear variable differential transformer (LVDT).

22. A method for determining rock properties, comprising:
exerting a compressive load with a test apparatus across a rock sample that comprises a specified length-to-diameter ratio;
measuring, with at least one strain gauge, a strain on the rock sample during the compressive loading, the at least one strain gauge coupled to an axial surface of the rock sample, the measuring comprising:
measuring an incremental axial strain on the rock sample during a compressive load increment with a first strain gauge; and
measuring an incremental radial strain on the rock sample during the compressive load increment with a second strain gauge;
determining, based at least in part on the compressive load, a mechanical property of the rock sample; and
determining, based at least in part on the measured strain and the compressive load, an elastic property of the rock sample, the determining comprising:
determining a Young's modulus of the rock sample based on at least one of:

$$E = \frac{\Delta P}{\Delta \varepsilon_x}(-F + \nu G), \quad \text{(i)}$$

where E is stress dependent Young's modulus of the rock sample, $\Delta P$ is the compressive load increment, $\Delta \epsilon_x$ is the incremental radial strain, $\nu$ is Poisson's ratio of the rock sample, F is a first coefficient, and G is a second coefficient; or $$E = \frac{P}{\varepsilon_x}(-F + \nu G), \quad \text{(ii)}$$

where E is Young's modulus of the rock sample, P is a particular compressive load, $\epsilon_x$ is a radial strain at the particular compressive load, $\nu$ is Poisson's ratio of the rock sample, F is the first coefficient, and G is the second coefficient.

23. A method for determining rock properties, comprising:
exerting a compressive load with a test apparatus across a rock sample that comprises a specified length-to-diameter ratio;
measuring, with at least one strain gauge, a strain on the rock sample during the compressive loading, the at least one strain gauge coupled to an axial surface of the rock sample, the measuring comprising:
measuring an incremental axial strain on the rock sample during a compressive load increment with a first strain gauge; and
measuring an incremental radial strain on the rock sample during the compressive load increment with a second strain gauge;
determining, based at least in part on the compressive load, a mechanical property of the rock sample; and
determining, based at least in part on the measured strain and the compressive load, an elastic property of the rock sample, the determining comprising:
determining Poisson's ratio of the rock sample based on at least one of:

$$\nu = \frac{\left(\frac{\Delta \varepsilon_x}{\Delta \varepsilon_y}\right) G + F}{\left(\frac{\Delta \varepsilon_x}{\Delta \varepsilon_y}\right) F + G}, \quad \text{(i)}$$

where $\nu$ is stress dependent Poisson's ratio of the rock sample, $\Delta \epsilon_x$ is the incremental radial strain, $\Delta \epsilon_y$ is the incremental axial strain, F is a first coefficient, and G is a second coefficient; or $$\nu = \frac{\left(\frac{\varepsilon_x}{\varepsilon_y}\right) G + F}{\left(\frac{\varepsilon_x}{\varepsilon_y}\right) F + G}, \quad \text{(ii)}$$

where $\upsilon$ is Poisson's ratio of the rock sample, $\epsilon_x$ is a radial strain at a particular compressive load on the rock sample, $\Delta\epsilon_y$ is an axial strain at the particular compressive load on the rock sample, F is the first coefficient, and G is the second coefficient.

24. A rock property test system, comprising:
a load cell configured to exert a compressive load across a rock sample;
at least one strain gauge positioned to measure a strain on the rock sample during the compressive loading, the strain gauge configured to attach to an axial surface of the rock sample and comprising a first strain gauge configured to measure an incremental axial strain on the rock sample during the incremental compressive load, and a second strain gauge configured to measure an incremental radial strain on the rock sample during the incremental compressive load; and
a control system communicably coupled to the load cell and the at least one strain gauge and configured to perform operations comprising:
controlling the load cell to exert an incremental compressive load on the rock sample;
receiving a measured strain on the rock sample, based on the incremental compressive load, from the at least one strain gauge;
determining, based at least in part on the incremental compressive load, a mechanical property of the rock sample; and
determining, based at least in part on the measured strain and the incremental compressive load, an elastic property of the rock sample, the determining comprising:
determining a first coefficient based at least in part on the diameter of the rock sample, the length of the rock sample, and an effective length of the first and second strain gauges;
determining a second coefficient based at least in part on the diameter of the rock sample, the length of the rock sample, and the effective length of the first and second strain gauges; and
determining the elastic property of the rock sample based at least in part on the measured incremental axial and radial strains on the rock sample, the first and second coefficients, and the incremental compressive load.

25. A method for determining rock properties, comprising:
exerting a compressive load with a Brazilian test apparatus across a rock sample that comprises a specified length-to-diameter ratio;
measuring, with the Brazilian test apparatus, a tensile strength of the rock sample based on the compressive load;
measuring, with a strain gauge that is coupled to an axial surface of the rock sample, a strain on the rock sample during the compressive loading, the measuring comprising:
measuring an incremental axial strain on the rock sample during a compressive load increment with a first strain gauge, and
measuring an incremental radial strain on the rock sample during the compressive load increment with a second strain gauge;
determining, based at least in part on the compressive load, a mechanical property of the rock sample; and
determining, based at least in part on the measured strains and the compressive load increment, a Young's modulus of the rock sample according to at least one of:

$$E = \frac{\Delta P}{\Delta \varepsilon_x}(-F + vG), \quad \text{(i)}$$

where E is stress dependent Young's modulus of the rock sample, $\Delta P$ is the compressive load increment, $\Delta\epsilon_x$ is the incremental radial strain, $\upsilon$ is Poisson's ratio of the rock sample, F is a first coefficient, and G is a second coefficient, or $$E = \frac{P}{\varepsilon_x}(-F + vG), \quad \text{(ii)}$$

where E is Young's modulus of the rock sample, P is a particular compressive load, $\epsilon_x$ is a radial strain at the particular compressive load, $\upsilon$ is Poisson's ratio of the rock sample, F is the first coefficient, and G is the second coefficient.

26. A method for determining rock properties, comprising:
exerting a compressive load with a Brazilian test apparatus across a rock sample that comprises a specified length-to-diameter ratio;
measuring, with the Brazilian test apparatus, a tensile strength of the rock sample based on the compressive load;
measuring, with a strain gauge that is coupled to an axial surface of the rock sample, a strain on the rock sample during the compressive loading, the measuring comprising:
measuring an incremental axial strain on the rock sample during a compressive load increment with a first strain gauge, and
measuring an incremental radial strain on the rock sample during the compressive load increment with a second strain gauge;
determining, based at least in part on the compressive load, a mechanical property of the rock sample; and
determining, based at least in part on the measured strains and the compressive load increment, a Poisson's ratio of the rock sample according to at least one of:

$$\upsilon = \frac{\left(\frac{\Delta \varepsilon_x}{\Delta \varepsilon_y}\right)G + F}{\left(\frac{\Delta \varepsilon_x}{\Delta \varepsilon_y}\right)F + G}, \quad \text{(i)}$$

where $\upsilon$ is stress dependent Poisson's ratio of the rock sample, $\Delta\epsilon_x$ is the incremental radial strain, $\Delta\epsilon_y$ is the incremental axial strain, F is a first coefficient, and G is a second coefficient; or $$\upsilon = \frac{\left(\frac{\varepsilon_x}{\varepsilon_y}\right)G + F}{\left(\frac{\varepsilon_x}{\varepsilon_y}\right)F + G}, \quad \text{(ii)}$$

where $\upsilon$ is Poisson's ratio of the rock sample, $\epsilon_x$ is a radial strain at a particular compressive load on the rock sample, $\Delta\epsilon_y$ is an axial strain at the particular compressive load on the rock sample, F is the first coefficient, and G is the second coefficient.

27. A rock property test system, comprising:
a load cell configured to exert a compressive load across a rock sample, the load cell comprising a Brazilian test apparatus;
at least one strain gauge configured to attach to an axial surface of the rock sample and positioned to measure a strain on the rock sample during the compressive loading, the at least one strain gauge comprising a first strain gauge configured to measure an incremental axial strain on the rock sample during the incremental compressive load and a second strain gauge configured to measure an incremental radial strain on the rock sample during the incremental compressive load; and
a control system communicably coupled to the load cell and the at least one strain gauge and configured to perform operations comprising:
controlling the load cell to exert an incremental compressive load on the rock sample;
determining a tensile strength of the rock sample based on the compressive load;
receiving a measured incremental axial strain on the rock sample and a measured incremental radial strain on the rock sample, based on the incremental compressive load, from the at least one strain gauge;
determining a first coefficient based at least in part on the diameter of the rock sample, the length of the rock sample, and an effective length of the first and second strain gauges;
determining a second coefficient based at least in part on the diameter of the rock sample, the length of the rock sample, and the effective length of the first and second strain gauges;
determining, based at least in part on the incremental compressive load, a mechanical property of the rock sample; and
determining, based at least in part on the measured strains and the incremental compressive load, a Young's modulus of the rock sample according to at least one of:

$$E = \frac{\Delta P}{\Delta\varepsilon_x}(-F + \nu G), \quad \text{(i)}$$

where E is stress dependent Young's modulus of the rock sample, $\Delta P$ is the compressive loading increment, $\Delta\epsilon_x$ is the incremental radial strain, $\upsilon$ is Poisson's ratio of the rock sample, F is a first coefficient, and G is a second coefficient; or $$E = \frac{P}{\varepsilon_x}(-F + \nu G), \quad \text{(ii)}$$

where E is Young's modulus of the rock sample, P is a particular compressive load, $\epsilon_x$ is a radial strain at the particular compressive load, $\upsilon$ is Poisson's ratio of the rock sample, F is the first coefficient, and G is the second coefficient.

28. A rock property test system, comprising:
a load cell configured to exert a compressive load across a rock sample, the load cell comprising a Brazilian test apparatus;
at least one strain gauge configured to attach to an axial surface of the rock sample and positioned to measure a strain on the rock sample during the compressive loading, the at least one strain gauge comprising a first strain gauge configured to measure an incremental axial strain on the rock sample during the incremental compressive load and a second strain gauge configured to measure an incremental radial strain on the rock sample during the incremental compressive load; and
a control system communicably coupled to the load cell and the at least one strain gauge and configured to perform operations comprising:
controlling the load cell to exert an incremental compressive load on the rock sample;
determining a tensile strength of the rock sample based on the compressive load;
receiving a measured incremental axial strain on the rock sample and a measured incremental radial strain on the rock sample, based on the incremental compressive load, from the at least one strain gauge;
determining a first coefficient based at least in part on the diameter of the rock sample, the length of the rock sample, and an effective length of the first and second strain gauges;
determining a second coefficient based at least in part on the diameter of the rock sample, the length of the rock sample, and the effective length of the first and second strain gauges;
determining, based at least in part on the incremental compressive load, a mechanical property of the rock sample; and
determining, based at least in part on the measured strains and the incremental compressive load, Poisson's ratio of the rock sample according to at least one of:

$$\upsilon = \frac{\left(\frac{\Delta\varepsilon_x}{\Delta\varepsilon_y}\right)G + F}{\left(\frac{\Delta\varepsilon_x}{\Delta\varepsilon_y}\right)F + G}, \quad \text{(i)}$$

where $\upsilon$ is stress dependent Poisson's ratio of the rock sample, $\Delta\epsilon_x$ is the incremental radial strain, $\Delta\epsilon_y$ is the incremental axial strain, F is a first coefficient, and G is a second coefficient; or $$\upsilon = \frac{\left(\frac{\varepsilon_x}{\varepsilon_y}\right)G + F}{\left(\frac{\varepsilon_x}{\varepsilon_y}\right)F + G}, \quad \text{(ii)}$$

where $\upsilon$ is Poisson's ratio of the rock sample, $\epsilon_x$ is a radial strain at a particular compressive load on the rock sample, $\Delta\epsilon_y$ is an axial strain at the particular compressive load on the rock sample, F is the first coefficient, and G is the second coefficient.

* * * * *